US006628376B1

(12) United States Patent
Nikitin et al.

(10) Patent No.: US 6,628,376 B1
(45) Date of Patent: Sep. 30, 2003

(54) METHOD OF EXAMINING BIOLOGICAL, BIOCHEMICAL, AND CHEMICAL CHARACTERISTICS OF A MEDIUM AND APPARATUS FOR ITS EMBODIMENT

(76) Inventors: Petr Ivanovich Nikitin, ul. Kargopolskaya, 10-287, Moscow, 127562 (RU); Andrei V. Kabashin, ul. Paustovskogo, 3-354, Moscow, 117463 (RU); Anatoly A. Beloglazov, ul. Profsojuznaya, 7/12-110, Moscow, 117218 (RU)

( * ) Notice: Subject to any disclaimer, the term of this patent is extended or adjusted under 35 U.S.C. 154(b) by 0 days.

(21) Appl. No.: 09/445,686

(22) PCT Filed: May 7, 1998

(86) PCT No.: PCT/RU98/00128

§ 371 (c)(1),
(2), (4) Date: Dec. 10, 1999

(87) PCT Pub. No.: WO98/57149

PCT Pub. Date: Dec. 17, 1998

(30) Foreign Application Priority Data

Jun. 11, 1997 (RU) .......................................... 97109315

(51) Int. Cl.[7] ................................................. G01N 1/00
(52) U.S. Cl. ................................................... 356/38
(58) Field of Search ..................... 356/36–39, 445–448, 356/451, 450, 517

(56) References Cited

U.S. PATENT DOCUMENTS 5,563,707 A * 10/1996 Prass et al. ................. 356/361

FOREIGN PATENT DOCUMENTS

| EP | 0305109 B1 | 1/1989 |
| EP | 0478137 | 4/1992 |
| GB | 2197068 | 5/1988 |
| GB | 2268800 A | 1/1994 |
| WO | WO 8907252 A1 | 8/1989 |

OTHER PUBLICATIONS

Nikitina, A N et al., "Phase Surface Plasmon Microscopy" vol. 17, No. 6, Jun. 1, 1991, pp. 418–419, XP000247542.
J.M. Simon, V. A. Presa: "Behaviour of the phases in the observation of surface electromagnetic waves" Journal of Modern Optics, vol. 36, No. 5, 1989, pp. 649–567, XP002079189.
Abeles et al., *Polaritons, Proceedings of the First Taormina Research Conference on the Structure of Matter*, pp. 241–247, (Oct., 1972).
Liedberg et al., *Sensors and Actuators*, vol. 4, pp. 299–304, (1983).

* cited by examiner

*Primary Examiner*—Tu T. Nguyen

(57) ABSTRACT

Examinations of biological, biochemical, and chemical characteristics of media, mainly of biologic origin, or media that are in contact with biological objects whose living is influenced by the media characteristics. One excites surface plasmon polaritons on a metal layer covered with a material sensitive to the examined characteristics of a medium, produces an interference with a beam of radiation reflected under these conditions and a reference beam, records parameters of a spatial intensity distribution in the resulting interference pattern, and judges the examined characteristics on the basis of the recorded parameters. The proposed method and apparatus ensure the technical result that consists in upgrading of sensitivity and resolution of measurements, at least, by two orders.

26 Claims, 5 Drawing Sheets

METHOD OF EXAMINING BIOLOGICAL, BIOCHEMICAL, AND CHEMICAL CHARACTERISTICS OF A MEDIUM AND APPARATUS FOR ITS EMBODIMENT

This application is the national phase under 35 U.S.C. §371 of PCT International Application No. PCT/RU98/00128 which has an International filing date of May 7, 1998, which designated the United States of America.

TECHNICAL FIELD

The invention refers to methods of examining biological, biochemical, and chemical characteristics of media, mainly of biological origin, or media that are in contact with biological objects whose living is influenced by the media characteristics.

BACKGROUND ART

In a known analogue [B. Liedberg, C. Nylander, and I. Lundstrom, Surface plasmon resonance for gas detection and biosensing, *Sensors and Actuators*, 4 (1983) 299–304] of the proposed method, a solution that contains an antigen is brought into contact with a thin layer of antibodies immobilised on a silver film adjacent to a glass prism. The film is exposed to laser radiation incident through the prism. Surface plasmon polaritons (SPP) are excited at the antibody layer-silver interface. One observes a resonant minimum in the reflected radiation intensity dependence on the angle of the radiation incidence on the film. The minimum is due to the pumping of radiation power into that of SPP. The interaction of the antigen and the antibody is recorded as a shift of the resonant contour of the dependence. The drawbacks of both the method and the apparatus of the analogue [B. Liedberg, C. Nylander, and I. Lundstrom, Surface plasmon resonance for gas detection and biosensing, *Sensors and Actuators*, 4 (1983) 299–304]. are associated with that it necessitates mechanical rotation units to scan and adjust the incidence angle, as well as to compensate for a displacement of the irradiation spot and to follow a rotation of the reflected beam. This makes the method and the apparatus cumbersome and unpractical, results in insufficient reliability, low accuracy of measurements, and weak sensitivity of the method.

In another analogue [WO 89/07252, G01N 21/17, 1989], radiation is fed into an optical waveguide with the output face bevelled at an angle that ensures the excitation of SPP at the interface of a sensitive layer and a metal film deposited on the face. The layer is capable of reacting with the medium component under test and changing by this means the conditions of the resonant SPP excitation. An information signal is extracted from the analysis of the radiation reflected back into the waveguide. The drawbacks of the analogue [WO 89/07252, G01N 21/17, 1989] are complexity of the method and the apparatus, connected with the techniques and means to analyse the output optical signal, and the need for selection of radiation modes and frequencies. These restrict the areas of application, lowers the accuracy of measurements and the sensitivity of the method.

The closest to the proposed invention is the analogue method of examining biological, biochemical, and chemical properties of media [EP 0 305 109 B1, G01N 21/55, 1993]. It comprises:

introducing a volume or a constituent of a medium under test into the region where it interacts with a sensitive material;

acting by electromagnetic radiation through a block transparent to the radiation on a metal layer located on a boundary surface of the block, said sensitive material being placed over the metal layer directly or on an intermediate material;

exciting surface plasmon polaritons by means of said acting;

reflecting partially said radiation from the surface of said metal layer, resulting in the formation of a beam of reflected electromagnetic radiation;

producing with said beam such a spatial distribution of electromagnetic field intensity that the distribution comprises features whose positions depend on the interaction of the medium under test with said sensitive material;

recording parameters of said distribution, from comparison of which with predetermined reference relationships the examined characteristics are judged.

The basis of the method is that in a spatial distribution of electromagnetic intensity that is formed using the reflected beam over an extended photodetector array there is a feature associated with the excitation of SPP, namely, a resonant intensity minimum. In a one-dimensional distribution, it is revealed as a dark band on the illuminated background area. The method of the analogue allows to record the spatial intensity distribution with the resonant contour of the reflectance minimum as a whole at every instant of time and obtain information on characteristics under study by the analysis of the position and the shape of the resonant contour. In so doing the method avoids mechanical rotations and displacements. Besides, the output signal is insensitive to radiation intensity drifts. The mentioned features are among important advantages of the analogue.

The main drawback of the analogue is low sensitivity of the output signal to variations in optical parameters of the sensitive material layer. This results in low resolution of the method. As reported in literature, such schemes enable one to achieve resolution no better than $3 \times 10^{-6}$ in terms of effective refraction index, and $10^{-8}$ in terms of albumin aHSA concentration detected by immunological binding HSA-aHSA directly on a gold surface. However, there is a number of problems in which lowering of a detection limit of biologically active components is of crucial importance. The example is hepatitis virus detection since even a single virus can cause infection. But, fundamental limitation on the prototype's resolution limit is imposed by the physical principle used, namely, sensitivity of the spatial position and/or the level of the reflected intensity minimum to variations in optical parameters of the sensitive material layer.

Besides, the detection of shifts of the position or the level of a resonant minimum involves the necessity to record all the resonant contour or the most part of it. The reason is that it is difficult to describe analytically the shape of the contour and actually impossible to find the position and the level of the minimum from few points of the contour. Thus, the detectability threshold of small shifts of the resonant contour is the lower, the greater is the spatial scale of the produced intensity distribution and the less is the size of each discrete element of the extended photodetector array. Since the angular width of the resonant contour is a fixed value defined by the physical mechanism of SPP excitation, lowering of the detectability threshold can be achieved only at the expense of increasing the spatial scale (and, consequently, the size of the photodetector array and the overall apparatus) or decreasing the size of each element of the array. Both approaches lead to a raise in the cost of the method and the apparatus, as well as to a fall in signal-to-noise ratio, and appear to be hardly acceptable.

Thus, the required technical result that eliminates the drawbacks of the known methods consists in rising the sensitivity and lowering the resolution threshold of the method, or, more concretely, in the following:

a) taking advantage of a superior physical principle to yield a parameter to be measured, which pertains to a spatial electromagnetic intensity distribution, so that the principle would ensure a higher sensitivity of this parameter to the characteristics of media under examination;

b) taking advantage of a more flexible technique to record small variations of said parameter, which would allow to lower the detectability threshold.

The known methods described above have been embodied in the apparatus for examining biological, biochemical, chemical characteristics of media. Their drawbacks are mentioned above as well as the required technical results eliminating them. The closest to the proposed apparatus is an analogue apparatus [EP 0 305 109 B1, G01N 21/55, 1993]. It comprises:

a source of electromagnetic radiation directed through a block transparent to the radiation on to a metal layer located on a boundary surface of said block so that there takes place a configuration for excitation of surface plasmon polaritons and partial reflection of said radiation from the surface of said metal layer, with formation of a reflected radiation beam;

a sensitive material placed over said metal layer directly or on an intermediate material;

a unit for introducing a volume or a constituent of a media under test into the region where it interacts with said sensitive material, the region being situated so that said interaction influences the properties of said surface plasmon polaritons and said reflected radiation beam;

a means for producing, with the use of said reflected radiation beam, a spatial electromagnetic field intensity distribution that contains features whose positions depend on said interaction;

a block for recording parameters of said distribution to obtain on its base an output information signal.

The known apparatus operates as follows. Radiation from a source is incident through a transparent block (which contains, for example, a glass prism and a glass slide in immersion contact) on a metal layer located on its boundary surface at the angle that ensures SPP excitation according to the frustrated total internal reflection configuration. On the metal surface there is a layer of a sensitive material. A volume or a constituent of the medium under analysis is introduced into contact with the sensitive material. All the arrangement is chosen so that the interaction of the medium under analysis with the sensitive material affects the properties of SPP and a beam that is formed due to a partial reflection of the incident radiation. Particularly, dependent of medium properties is the complex wavevector of SPP, which determines the position and the shape of a resonant contour with a minimum in the angular dependence of the reflected radiation intensity. To record the resonant contour, in the prototype apparatus one employs a means for producing a spatial intensity distribution with the use of the reflected radiation beam. The means comprises components to specify the spatial width of the incident radiation beam and to focus the beam on the metal layer so that a range of incidence angles is provided, that embraces the resonant contour or its part. After a partial reflection, a divergent beam is formed, which comes to a photodetector that is capable of receiving a range of angles necessary for obtaining information on medium characteristics under test from the features of the resonant contour of the reflected radiation intensity. The example is an extended photodetector array that consists of a large number of discrete photosensitive areas (pixels), where the position of the resonant minimum of the reflected beam intensity is expressed as the number of such an area (pixel). The information yield is obtained from the analysis of the position or/and the level of the resonant intensity minimum.

The known apparatus has the drawbacks described in detail above, in the discussion on the known method. Briefly, they can be summarised as low sensitivity and insufficient resolution. Besides, as the angular width of the resonant contour is fixed, to lower the resolution threshold of the shifts of the spatial intensity distribution one has to enlarge the size of the photodetector array and the overall apparatus, as well as the number of photosensitive pixels with decreasing their size. This leads to a dramatic raise in the cost of the apparatus and a fall in a signal-to-noise ratio.

DISCLOSURE OF INVENTION

To achieve the technical result stated above, there is proposed a method of examining biological, biochemical, chemical characteristics of media, including characteristics of media interactions with surfaces and superficial layers, which comprises:

introducing a volume or a constituent of a medium under test into the region where it interacts with a sensitive material;

acting by electromagnetic radiation through a block transparent to the radiation on a metal layer located on a boundary surface of the block, said sensitive material being placed over the metal layer directly or on an intermediate material;

exciting surface plasmon polaritons by means of said acting;

reflecting partially said radiation from the surface of said metal layer, resulting in the formation of a beam of reflected electromagnetic radiation;

producing with said beam such a spatial distribution of electromagnetic field intensity that the distribution comprises features whose positions depend on the interaction of the medium under test with said sensitive material;

recording parameters of said distribution, from comparison of which with predetermined reference relationships the examined characteristics are judged;

in a manner like the analogue.

The proposed method differs in that said distribution is produced using interference of said beam and, at least, one more beam of electromagnetic radiation, which differs from the former beam in position and/or direction in space anywhere over its preceding propagation path.

In addition, said distribution may be produced with two beams reflected from the surface of said metal layer so that the properties of only one of the beams depend on the interaction of the medium under test with said sensitive material.

In addition, both said beams may be formed under conditions of surface plasmon polariton excitation.

In addition, one may use non-monochromatic radiation with a discrete and/or continuous set of frequencies inherent in said radiation, and parameters of said distribution may be recorded at a number, or within a band, of frequencies that belong to said set.

In addition, said beam contains radiation components with mutually orthogonal polarisation directions and said distribution is produced using interference of the beams comprising said components.

In addition, said electromagnetic radiation acting on said metal layer is shaped as a divergent or convergent beam.

The method described above has been embodied in a proposed apparatus for examining biological, biochemical, chemical characteristics of media, including characteristics of media interactions with surfaces and superficial layers. It eliminates the mentioned drawbacks of the analogue apparatus, and comprises:

- a source of electromagnetic radiation directed through a block transparent to the radiation on to a metal layer located on a boundary surface of said block so that there takes place a configuration for excitation of surface plasmon polaritons and partial reflection of said radiation from the surface of said metal layer, with formation of a reflected radiation beam;
- a sensitive material placed over said metal layer directly or on an intermediate material;
- a unit for introducing a volume or a constituent of a media under test into the region where it interacts with said sensitive material, the region being situated so that said interaction influences the properties of said surface plasmon polaritons and said reflected radiation beam;
- a means for producing, with the use of said reflected radiation beam, a spatial electromagnetic field intensity distribution that contains features whose positions depend on said interaction;
- a block for recording parameters of said distribution to obtain on its base an output information signal;

in a manner like the analogue.

The proposed apparatus differs from the analogue in that said means for producing a spatial electromagnetic field intensity distribution comprises a facility for separating radiation into; at least, two beams, a first of them comprising radiation that participates in the formation of said reflected radiation beam, and a second one differing from the first beam in position and/or direction in space, as well as a facility for bringing radiation from said first beam and from said second beam to an area where interference of radiation from these beams occurs, the position of said block for recording parameters of said distribution being appropriate to the position of said area of interference.

Besides, the apparatus is made so that it is allowed to vary the angle that defines the direction of radiation from said source of electromagnetic radiation with respect to said metal layer. This is necessary for the adjustment at an operation point of the incidence angle or recording the resonant contour of the angular dependence of reflected beam intensity.

Besides, said source of electromagnetic radiation may allow to specify a discrete or continuous set of frequencies of the outgoing radiation, and said block for recording parameters of said distribution may allow to perform said recording at a number, or within a band, of frequencies that belong to said set. This is appropriate for recording resonant features of reflected beam intensity against frequency rather than incidence angle. In particular, this enables one to realise a combined regime, in which observing an interference pattern at a specified frequency within the resonance ensures high sensitivity and recording the resonant contour against frequency does wide dynamic range of measurements.

Besides, the elements of the apparatus may be arranged so that there are two interfering, with each other or with other beams as well, beams reflected from said metal layer so that the interaction of the medium under analysis with said sensitive material influences only one of the two said radiation beams, and each of participating in said interference radiation beams differs from other ones in position and/or direction in space. In particular, each of the two beams may be reflected from the metal layer under SPP excitation. In this case, the beams should be arranged so that only one of them undergoes reflection with SPP excitation at the interface of the metal and a sensitive material exposed to a medium under analysis. The use of two beams reflected from the same metal layer for their interference between each other or with a third beam enables one to reduce the influence of parasitic effects due to mechanical and/or temperature instabilities.

Besides, said facility for separating radiation is designed so as to yield said first and said second beam, with polarisation directions orthogonal to each other. In particular, there is a polariser (analyser) or a polarisation rotation means across, at least, one of said first and said second beam.

Besides, said source of electromagnetic radiation is designed so as to supply a divergent or convergent radiation beam on to said metal layer.

MODES FOR CARRYING OUT THE INVENTION

Figure 1:
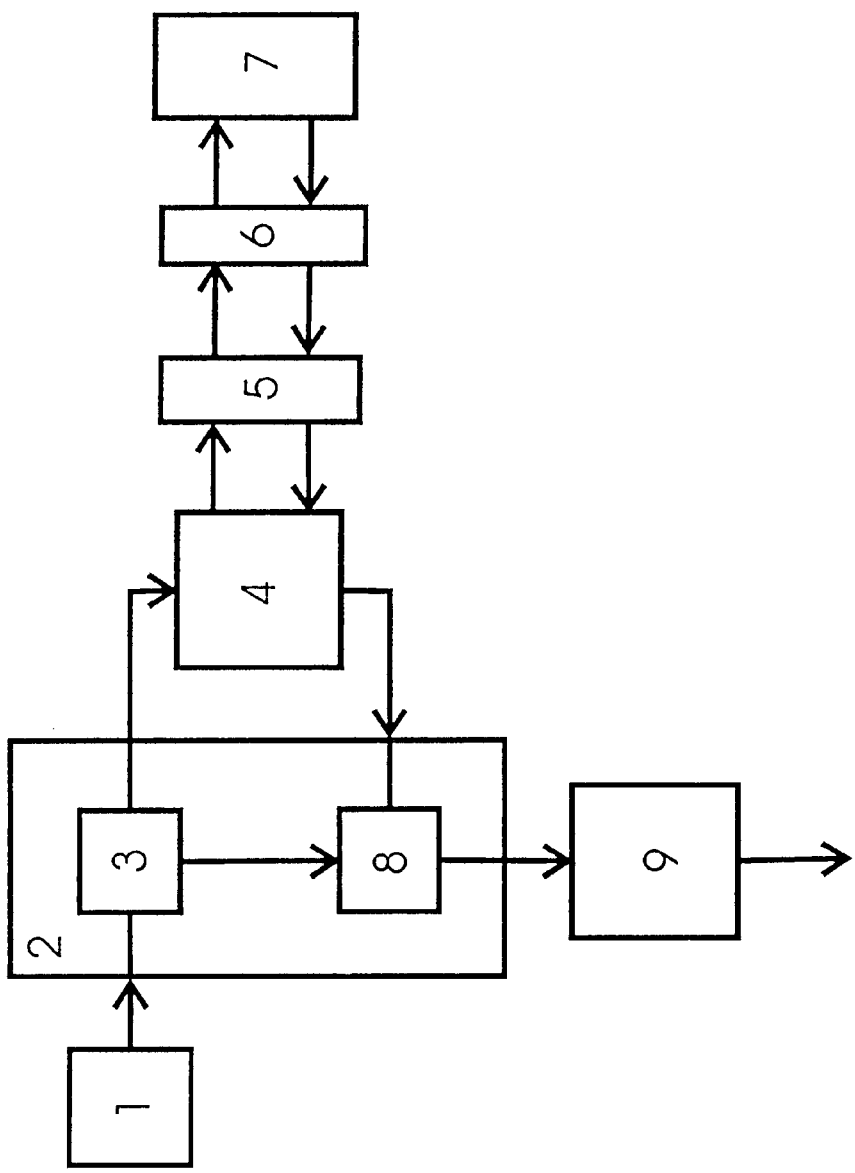
FIG. 1. Schematic drawing of an apparatus that embodies the proposed method.

A schematic drawing of the apparatus that embodies the proposed methods is given in FIG. 1 with the following notations: 1—a radiation source; 2—a means to produce a spatial intensity distribution; 3—a facility for providing SPP-active and inactive radiation components; 4—a transparent block; 5—a metal layer; 6—a sensitive material; 7—a unit for introducing a medium under test; 8—a facility for bringing the radiation to an interference area; 9—a block to record parameters of the spatial intensity distribution.

Figure 2:
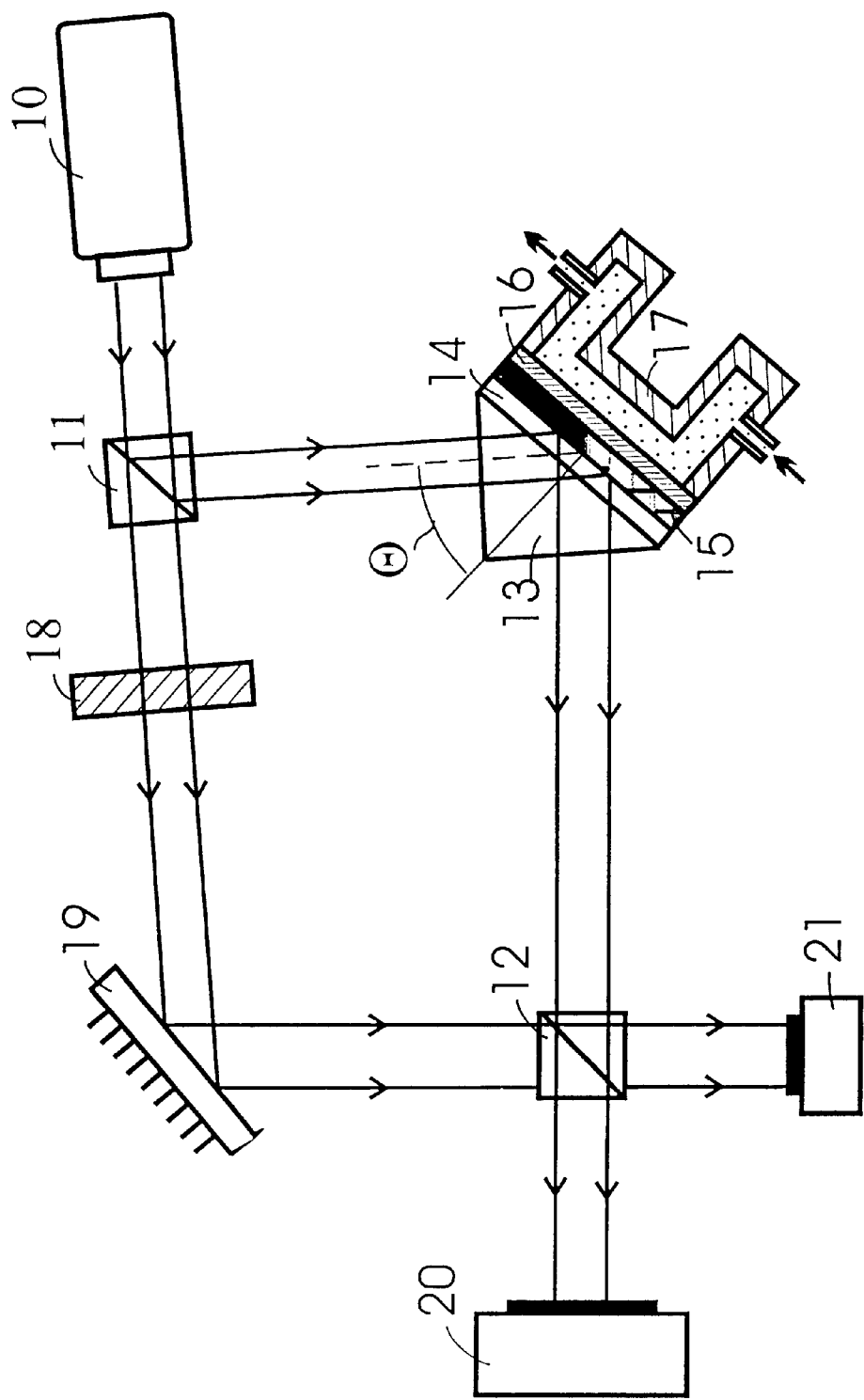
FIG. 2. Variant of an apparatus that embodies the proposed method.

A variant of the apparatus that embodies the proposed method is shown in FIG. 2. The notations are as follows: 10—a helium-neon laser; 11, 12—beam-splitting cubes; 13—a glass prism; 14—a glass slide; 15—a gold film; 16—a layer of antibodies; 17—a micro-cell with the flow of an antigen-containing solution; 18—a light-absorbing filter; 19—a mirror; 20—a CCD matrix; 21—a wide-aperture photodiode.

Figure 3:
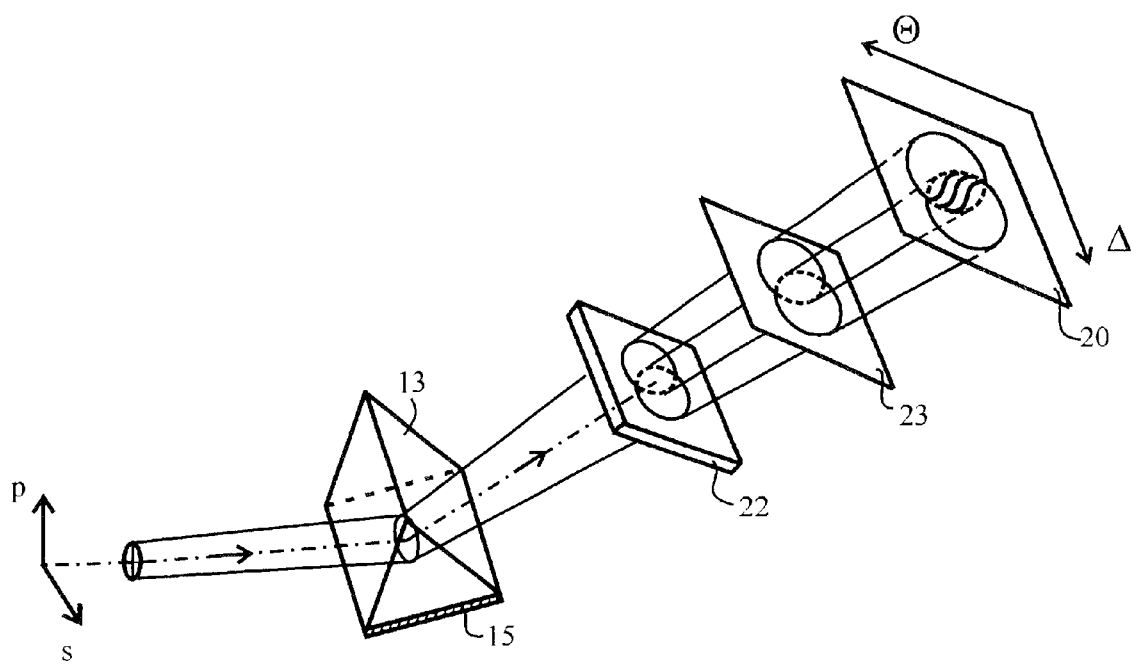
FIG. 3. Variant of the apparatus that embodies the proposed method and uses s- and p- polarised components of the radiation.
Figure 4:
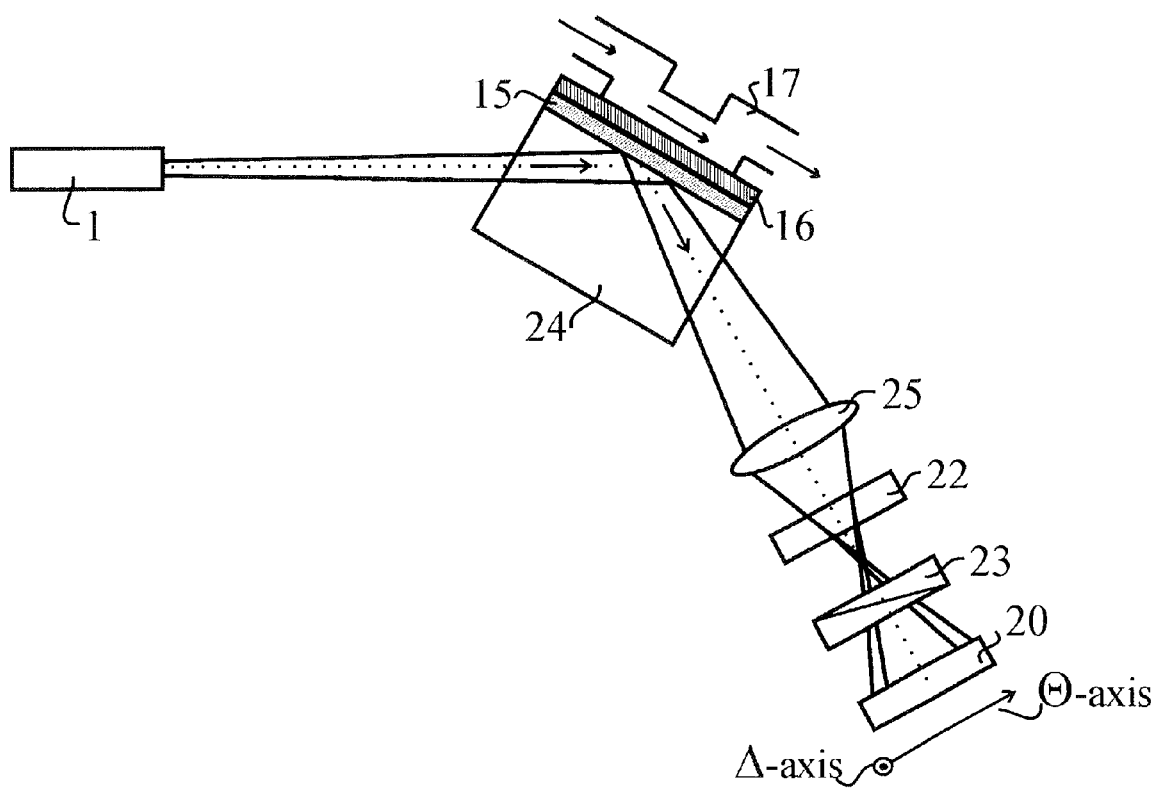
FIG. 4. Scheme of the apparatus that embodies the proposed method and uses orthogonally polarised (s- and p-) radiation components.

Variants of the apparatus that embodies the proposed method and uses s- and p-polarised radiation components are given in FIGS. 3, 4. The notation are as follows: 22—s- and p-polarisation splitter; 23—analyser; 24—transparent block (e.g. cube); 25—lens.

The dependencies of reflectivity R (a) and phase shift $\Delta$ (b) upon angle of radiation incidence $\Theta$ are shown in FIG. 5 for different thickness of a silver film: curves 25, 27–50 nm; curves 26, 28–55 nm.

Several variants of the proposed method and apparatus are realised (see FIGS. 1–4) for examining biological, biochemical, chemical characteristics of media, including characteristics of media interactions with surfaces and superficial layers.

The physical principle that forms the basis of the proposed method is that the information on examined characteristics of a medium and its interaction with a sensitive material placed on the surface of a SPP-supporting metal layer is carried by both the amplitude of the electromagnetic wave reflected from the metal layer under SPP excitation conditions and the phase of this wave [F. Abeles and T. Lopez-Rios, Ellipsometry with surface plasmons for the investigation of superficial modifications of solid plasmas. In book "Polaritons". Proceedings of the First Taormina Research Conference on the Structure of Matter, Oct. 26, 1972, Taormina, Italy, edited by E. Burstein and F. de Martini (Pergamon Press, New York, 1974), pp. 241–246.]. Therefore, in the proposed method one produces a spatial intensity distribution, whose parameters are served to judge the examined medium characteristics, in such a way that the distribution accounts for not only the amplitude of the mentioned reflected wave, like the analogue, but, what is the fundamental difference, its phase as well. The means that realises the principle is the interference of the mentioned wave and another, reference, wave.

Let us explain the operation principle of the proposed method, considering the variant of an apparatus that embodies the proposed method, which is shown in FIG. 2.

For example, a biologic solution is analysed for the presence of an antigen. For this purpose, some volume of the solution under analysis is introduced into a micro-cell 17 where it interacts with the layer of a sensitive material 16. In the scheme of FIG. 2 this material is an antibody that binds complementarily the corresponding antigen. As a result, there occurs a growing of the effective thickness of the layer 16. Other types of interactions can modify also the index of refraction and/or extinction of the layer 16. In case of insufficient selectivity of the interaction of the layer 16 with a multi-component medium, only a constituent of interest can be introduced into the region of the interaction with the layer, for example, by passing through a selecting membrane. The sensitive material 16 is placed on the surface of a metal layer 15 characterised by little damping of SPP, most commonly silver or gold. The material 16 may be deposited on the surface of the metal 15 directly or with an intermediate material. Such a material can be, for example, a thin dielectric layer on silver to prevent degradation of the latter, or protein molecules bound with gold for immobilisation of antibodies on them.

Figures 5A, 5B:
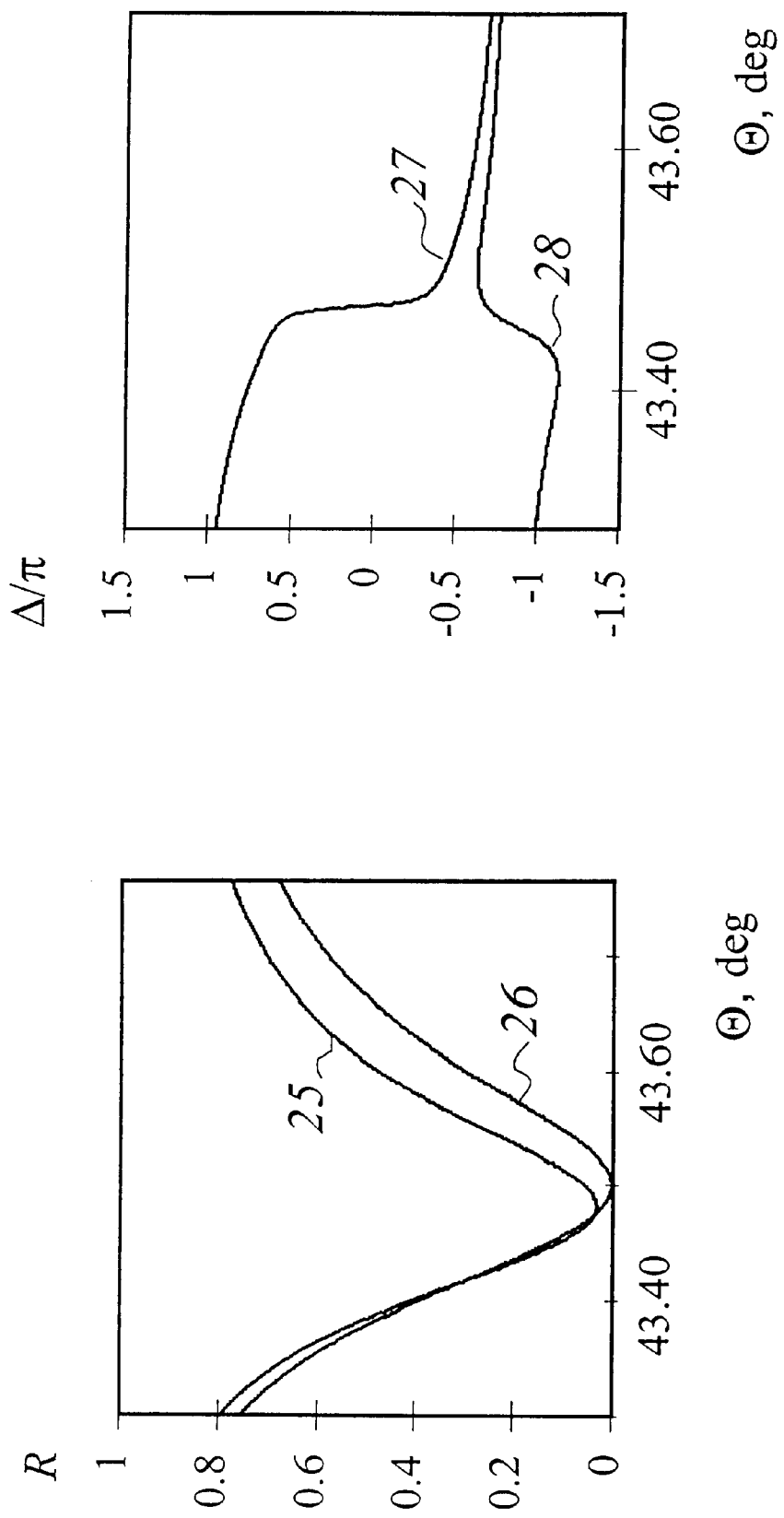
FIG. 5. Dependence of reflectivity R ($a$) and phase shift $\Delta$ ($b$) upon angle of radiation incidence $\Theta$ for different thickness of a SPP-supporting silver film.

The metal layer 15 is exposed to radiation polarised in the incidence plane (p-polarised), which falls from a source (for example, a helium-neon laser 10 in FIG. 2) through a transparent block, a boundary surface of which is adjacent to the surface of the layer 15 (in FIG. 2 such a block consists of a glass prism 13 and a slide 14 in immersion contact with each other). The combination of the layer 15 and the mentioned block is necessary for SPP excitation at the interface of the layers 15 and 16 by the so-called frustrated total internal reflection technique, because it is this combination that allows to match the wavevectors of radiation and SPP at a definite angle of radiation incidence on the layer 15. The presence of the matching condition implies that the energy of the incident radiation is converted to that of SPP and finally absorbed by the metal in a resonant manner. Consequently, near the indicated incidence angle there take place resonant angular dependencies of both amplitude and phase of the complex reflection coefficient of a radiation wave field. The dependence of the amplitude appears as a bell-like resonant contour (FIG. 5a) with a reflectance minimum (theoretically, zero at the optimum thickness of the metal layer 15). The dependence of the phase has the shape of a "step" with a phase drop within the contour up to $2\pi$ and the steepest slope at the position of the minimum (FIG. 5b). The slope steepness depends strongly on how close to the optimum is the thickness of the layer 15. The complex wavevector of SPP and hence the position and the shape (width and minimum level) of the resonant contour depend strongly on the optical characteristics of the layer 16 (thickness, refraction and extinction indices), which, in turn, are affected by the examined characteristics of the medium through the interaction with the latter. Thus both the amplitude and the phase of the beam formed as the result of the partial reflection of the radiation from the metal layer 15 carry information on the examined characteristics of the medium.

The read-out of the information carried by the phase of the reflected wave is provided for in the proposed method by producing a spatial electromagnetic intensity distribution dependent on the phase, and recording parameters of the distribution, from comparison of which with predetermined reference relationships the examined characteristics are judged. This approach enables one to avoid the influence of radiation intensity drifts on the information signal. One of the methods to produce a desired spatial distribution is the interference of the reflected wave (as a signal wave) and some reference wave, the information source being the shift of interference fringes. The sensitivity of the information signal to variations in the medium parameter under analysis is expressed in terms of the rate of the shift of interference fringes and defined by the steepness of the "step" slope of a relevant resonant dependence of the phase of a complex reflection coefficient (FIG. 5b). The interference is obtained by means of a spatial separation of the radiation from a single source into, at least, two beams, followed by their bringing to the area of the interference. To do this, two beam-splitting cubes 11, 12, and a mirror 19 are served in the scheme of FIG. 2. Besides, a filter 18 is used to provide a desirable contrast of the interference pattern by matching field amplitudes of the reference and signal waves, taking into account that the reflection coefficient amplitude of the latter is near the minimum. The position of the mirror 19 determines the convergence angle between the signal and reference beams and, hence, the period of the interference pattern within the interference area. Parameters of the intensity distribution in the interference pattern are registered by an extended photodetector array, for example, a CCD matrix 20. An auxiliary wide-aperture photodiode may be introduced into the scheme to follow the position of an operating point on the resonant contour of the reflection coefficient amplitude.

The mentioned difference from the analogue method, namely, that information on the medium characteristics under analysis is contained in the recorded spatial intensity distribution owing to the account for the phase of the signal reflected wave, and that the distribution itself is an interference pattern that allows to tune it to the desirable interval between neighbour maxima or minima,—determines the advantages of the proposed method and enables one to eliminate the drawbacks of the analogue.

Indeed, a much higher sensitivity of the phase of a signal wave, as compared to its amplitude, to the conditions of resonant SPP excitation and hence to the medium characteristics under examination results in a drastic increase in sensitivity and a lowering of resolution threshold. This has been demonstrated not only by calculations but by a model experiment as well. In the scheme of FIG. 2 a bare gold film without layer 16 was used, for which a resonant reflected intensity minimum under SPP excitation was observed at the level of 5%, the half-width of the resonant contour being about 1.2°. Pure gases, argon and nitrogen, were made to alternately flow through the cell 17. The refraction indices of the gases differ by $1.5 \times 10^{-5}$ under normal conditions. This difference led to the shift of interference fringes, that corresponded to the change in the phase of the signal wave by $0.77\pi \times$. It is known that in conventional interferometry one can easily obtain the phase resolution at the level of $2\pi \times 10^{-3}$ and better. The last value implies the resolution of the proposed method to be $4 \times 10^{-8}$ or better in terms of refraction index, that is two orders better than the capability of the analogue method.

To achieve such a high resolution, another advantage of the proposed method over the analogue is also important, namely, much more flexibility in the measurements of small shifts of interference fringes. Indeed, as the spatial intensity distribution in an interference pattern is characterised merely by a sinusoid, one can easily calculate analytically the overall shift of the pattern from changes even in a small portion of the sinusoid. Furthermore, in contrast to the analogue where the width of the resonant contour is a constant value and specifies the scale of a spatial intensity distribution to be recorded, in the proposed method one can set the scale of an interference pattern merely by choosing the convergence angle between a signal and a reference beam. Hence, to record even a very little shift of an interference pattern, one can choose a very large scale of the pattern so that the size of the whole photodetector array covers only a small fraction of the above mentioned sinusoid, whereas the change in the signal from this array, that corresponds to a shift of the whole pattern, is yet detectable over the noise level.

One can see that the method of measuring media parameters, which is based on recording of solely one interference pattern, is characterised by a limited dynamic range. Namely, only those parameter values are registered which do not move the system off the slope of the "step" of a resonant phase dependence. However such a difficulty is easy to overcome by a combined technique in which one achieves the extremely high resolution mentioned above with the use of an interference pattern, and a wide dynamic range by traditional recording of a resonant dependence of a reflection amplitude. The simplest means to do so is a photodiode 21 in the scheme of FIG. 2.

Another possibility for doing so is recording a resonant dependence of reflection amplitude on radiation frequency rather than on incidence angle. For this purpose, it is reasonable to employ a non-monochromatic radiation source bearing a discrete or/and a continuous set of frequencies, and to record spatial intensity distribution parameters at a number, or within a band, of frequencies of the set. In particular, a scheme exploiting a radiation source with a spectral width matching the spectral width of the resonant contour is thought to be promising. By passing the radiation reflected from a metal layer with SPP excitation through a dispersion element (a prism or a diffraction grating), one can observe a resonant contour of reflected intensity against radiation frequency along the direction perpendicular to the incidence plane. With the use of a two-dimensional photodetector array one can provide for a regime, in which precise and high-resolution measurements of the medium characteristics under test (e. g., detection of ultra-low concentrations of a bio-reagent in a solution) are carried out by recording an interference pattern along one co-ordinate of the array at a specified frequency, and more rough measurements (respectively, at relatively high concentrations of the reagent) are done by observing a resonant intensity contour against frequency along the other co-ordinate.

To avoid unwanted possibilities of relative displacements of a signal and a reference beam, both beams can be reflected from the surface of said metal layer so that the properties of only one of them depend on the interaction of the medium under analysis with a sensitive material on the surface of the layer. This results if the signal beam is directed on a metal area that is covered with the sensitive material, and the reference beam falls beyond this area. Furthermore, both beams may be reflected under SPP excitation conditions to maximally compensate for parasitic drifts of the interference pattern, which can result from mechanical or temperature instabilities. The mentioned two beams reflected from the metal layer may interfere either with each other or with a third beam, each in its own area of interference. In the latter case, one records not an absolute but a relative shift of two interference patterns.

The facility for a spatial separation of the radiation into two or more beams can be, for example, a partially reflecting plate or a beam-splitting cube or a number of such elements in the variant of the proposed apparatus shown on FIG. 2. The bringing of the beams to the area of interference can be provided by a beam-splitting cube (FIG. 2), mirrors, facilities such as a Fresnel binary prism, etc. The adequate means for recording parameters of an interference pattern is an extended photodetector array such as a photodiode array or a CCD matrix. As discussed above, the resulting apparatus enables one to achieve the resolution, at least, two orders better as compared to the prototype. To achieve such a resolution, it is important to be able to pre-set the period of the interference pattern and, hence, the scale of the analysed spatial intensity distribution by adjusting the convergence angle between the interfering beams at the desirable value. This can be done by a simple adjustment of a beam-directing mirror (element 19 in FIG. 2).

Next variants of the method and apparatus which provide both an ultra-high sensitivity and a wide dynamic range are shown in FIGS. 3, 4. Two orthogonal polarisation components of the same incident divergent beam of electromagnetic radiation are allowed to interfere. The p-polarised (polarisation lying in the incidence plane) radiation couples with the SPP and carries the information of interest. At the same time, the s-polarised (the polarisation orthogonal to the radiation incidence plane) component is unaffected by the SPP and serves as a reference beam. The principle is embodied in the experimental schemes displayed in FIGS. 3, 4. Both p- and s-polarisation components are in the divergent radiation beam that is reflected from a metal (gold or silver) film 15. SPP at the outer surface of the film are excited with the aid of a prism 13 or transparent block 24 by a beamlet at the incidence angle within surface plasmon resonance (SPR) conditions. After the reflection, the beams with the orthogonal polarisations are separated (shifted with respect to each other) by means of a birefringent crystal plate or another s-, p-polarised components splitter -22. The direction of the shift lies out of the SPR incidence plane and can be varied by rotating the plate 22. The two resulting beams are allowed to pass through an oblique analyser 23 and to interfere on the surface 20 of a two-dimensional CCD or photodetector matrix. The ratio of p- and s-polarisation intensities in the radiation beam incident onto the prism 13 or block 24 (cube) is adjusted so as to produce a desirable contrast of the interference pattern on the surface 20. (The means that provides the p- and s-polarisation components with desirable intensities is shown in FIG. 1 under the number 3.) The intersection of the SPR incidence plane and the surface 20 is a line that serves as the coordinate axis of the incidence angle θ. The direction of the beam shift by the plate 22 indicates the coordinate axis of the phase difference Δ between s- and p-polarised reflected beams on the surface 20. When the shift is perpendicular to the SPR incidence plane, the axes are perpendicular to each other. In this coordinate system, an interference fringe is the image of the dependence of Δ on θ. When the shift is parallel to the SPR incidence plane, the interference fringes are merely straight lines perpendicular to that plane, similarly to the patterns observed with the apparatus shown in FIG. 2.

The advantages of the imaging scheme pictured in FIG. 3 are compactness and immunity to parasitic noises and drifts thanks to that the interfering beams pass through the same optical elements. The described principle is compatible with the SPR sensor designs, which employ either a convergent or divergent radiation beam incident onto the metal film. (For definiteness, only the divergent incident beams are shown in FIGS. 3, 4.) Besides, the principle is applicable not only to the prism SPR configurations, but grating ones as well.

The shapes of the interference fringes have a well-marked bend, which corresponds to the "step" of a resonant phase dependence (FIG. 5*b*). A clear resonant minimum of the reflected intensity can be seen in the interference pattern as a dark zone that goes along the vertical direction across the fringes and intersects them at the bend. The angular position of the phase "step" coincides with that of the reflected intensity minimum. Besides, the shapes of the fringes are different for the cases when the thickness of a metal film is less (curve 27 in FIG. 5*b*) and greater (curve 28 on FIG. 5*b*) than the optimum value (about 52 nm for silver in air and He-Ne laser radiation). The sign of the "step" slope is also different in the two cases as shown in FIG. 5*b*. The inversion of the "step" occurs when the metal film thickness increases passing the optimum. The inversion is observed while scanning the illuminated spot over the surface of an inhomogeneous metal film along the gradient of its thickness. In biosensing the inversion can result from a growth of the thickness of a bio-receptor layer on the metal surface.

The described method and apparatus of the phase imaging against incidence angle applies to biosensing. For this purpose, the interference pattern produced as shown in FIG. 4 is monitored during the binding reaction of an antibody with an antigen in order to detect the latter in a solution. The antigen is 2,4-D pesticide. The antibodies for a specific binding are taken from rabbit anti-2,4-D serum. The antibodies are immobilized by means of the Langmuir-Schaefer technique on a gold film deposited on the prism and placed in the flow of the pesticide aqueous solution of a predetermined concentration.

A slight inhomogeneity of the antibody layer over the slide surface can be used for choosing of the working area on the surface. Namely, the spot illuminated by the incident beam can be positioned so that the conditions of radiation-to-surface plasmon coupling are very close to the optimum, and even little binding causes the system to pass through the optimum. This results in dramatic changes of the interference pattern. The evolution of the pattern accompanied by the inversion of the "step" is observed as a result of binding of 2,4-D in a $10^{-10}$ M/l aqueous solution and the antibodies taken from rabbit anti-2,4-D serum No SPR angular shift of the reflected intensity minimum is observed for such small 2,4-D concentration. This means that the monitoring of the "step" inversion is much more sensitive to a surface binding than the traditional SPR methods, other conditions being equal.

The phase "step" can displace with the intensity minimum and serve as its sharp marker which enables one to measure the SPR shift with a higher accuracy. Measuring the shift provides for the dynamic range of the described technique as wide as that of traditional SPR methods.

The proposed SPR interferometry method and apparatus open up the possibilities for the sensors that combine both ultra-high sensitivity to a (bio)chemical analyte and wide dynamic range. The technique offers three information sources and, respectively, three levels of sensitivity. The highest sensitivity and operation at the lowest analyte concentrations are provided by the monitoring of the "step" inversion. A lower level of phase sensitivity, which is yet higher than that of traditional SPR intensity measurements [EP 0 305 109 B1, G01N 21/55, 1993], relates to the steepness of the "step". The sensor response at this level can be quantified by the tangent of an interference fringe slope at the resonant bend, if the shift between interfering beams in the scheme of FIG. 4 lies out of the SPR incidence plane. If the shift is parallel to that plane, the response can be revealed by the displacement of the straight fringes, like with the apparatus shown in FIG. 2. The lowest sensitivity and operation at highest concentrations can be realised by the measurement of a SPR angular shift just as it is usually done in the traditional SPR sensors. The dynamic range is limited only by the angular spread of the reflected beam received by a two-dimensional photodetector.

In conclusion, it has been shown that the required technical result is achieved owing to considerable distinctions of the proposed apparatus.

INDUSTRIAL APPLICABILITY

The invention can be put to use in the identification of composition and properties of media containing biological and chemical components for the purposes of fundamental research and applications in microbiology, immunology, medicine, biochemistry, as well as for environmental monitoring. In particular, it applies to detection of biologically active components and measurement of their concentrations when combined with immunoassay methods and allows to monitor interactions of antibodies with corresponding antigens in realtime regime.

What is claimed is:

1. A method of examining biological, biochemical, chemical characteristics of media, including characteristics of media interactions with surfaces and superficial layers, which comprises:

introducing a volume or a constituent of a medium under test into contact with a sensitive material;

acting by electromagnetic radiation through a transparent body on a metal layer located on a boundary surface of the body, said sensitive material being placed on said boundary surface above the metal layer directly or through an intermediate material;

providing a surface plasmon resonance by means of said acting;

reflecting partially said radiation under said surface plasmon resonance from said metal layer, with formation of a reflected beam;

using said reflected beam for producing a spatial distribution of electromagnetic field intensity, which is determined by said surface plasmon resonance;

recording parameters of said distribution, from which the examined characteristics are judged;

wherein said distribution, at a number or within a band of frequencies chosen among the frequencies in said radiation, is produced using interference of said reflected beam and, at least, one more radiation beam, which differs from said reflected beam in position or direction in space anywhere over its propagation path preceding to the interference.

2. A method according to claim 1, wherein a user controls sensitivity of parameters of said distribution to the interaction of the medium under test with said sensitive material by choosing a frequency or frequencies of the radiation at said number or within said band of frequencies, at which parameters of said distribution are recorded.

3. A method according to claim 1, wherein said interference occurs at a plane where the phase difference between two beams participating in said interference undergo rapid changes along different directions which are orthogonal or tilted to each other.

4. A method according to claim 1, wherein said interference occurs at a plane where the angle of incidence of said radiation on said metal layer and the phase difference between two beams participating in said interference undergo rapid changes along different directions which are orthogonal or tilted to each other.

5. A method according to claim 1, wherein in said distribution there are provided two different directions which can serve as co-ordinate axes, orthogonal or tilted to each other, such that the phase difference between two beams participating in said interference undergoes rapid change along one direction and along the other direction there occurs a rapid change of a first parameter relevant to said surface plasmon resonance, and the interaction of the medium under test with said sensitive material is monitored by a change of the slope, or the sign of the slope, of interference fringes within said distribution near the value of said first parameter that corresponds to said surface plasmon resonance, with respect to said co-ordinate axes.

6. The method of claim 5, wherein said change is selected from the group consisting of frequency of said radiation, angle of incidence of said radiation on said metal layer, and thickness of a layer on said boundary surface.

7. A method according to claim 1, wherein said distribution comprises two directions which can serve as co-ordinate axes, orthogonal or tiled to each other, such that the phase difference between two beams participating in said interference undergoes a rapid change along one direction and along the other direction there occurs a rapid change of a first parameter relevant to said surface plasmon resonance and a user uses a variation in a second parameter, different from said first parameter and relevant to said surface plasmon resonance, to approach a value of said second parameter, at which interference fringes within said distribution change the sign of the slope of the interference fringes near the value of said first parameter that corresponds to said surface plasmon resonance or have no distinct sign under transition from one sign of the slope to the other, with respect to said co-ordinate axes.

8. The method of claim 7, wherein said change is selected from the group consisting of frequency of said radiation, angle of incidence of said radiation on said metal layer, and thickness of a layer on said boundary surface.

9. The method of claim 7, wherein said variation is selected from the group consisting of frequency of said radiation, angle of incidence of said radiation on said metal layer, and thickness of a layer on said boundary surface.

10. A method of examining biological, biochemical, chemical characteristics of media, including characteristics of media interactions with surfaces and superficial layers, which comprises:

introducing a volume or a constituent of a medium under test into contact with a sensitive material;

acting by electromagnetic radiation through a transparent body on a metal layer located on a boundary surface of the body, said sensitive material being placed on said boundary surface above the metal layer directly or through an intermediate material;

providing a surface plasmon resonance by means of said acting;

reflecting partially said radiation under said surface plasmon resonance from said metal layer, with formation of a reflected beam;

using said reflected beam for producing a spatial distribution of electromagnetic field intensity, which is determined by said surface plasmon resonance;

recording parameters of said distribution, from which the examined characteristics are judged;

wherein said distribution is produced using interference of, at least, two beams, said reflected beam and a second radiation beam reflected from said metal layer, said second beam differing from the rejected beam in position or direction in space anywhere over its propagation path preceding to the interference.

11. A method according to claim 10, wherein said radiation includes two components with mutually orthogonal polarization directions, and said distribution is produced using interference of said two beams, each beam comprising one of said components.

12. A method of examining biological, biochemical, chemical characteristics of media, including characteristics of media interactions with surfaces and superficial layers, which comprises:

introducing a volume or a constituent of a medium under test into contact with a sensitive material;

acting by electromagnetic radiation through a transparent body on a metal layer located on a boundary surface of the body, said sensitive material being placed on said boundary surface above the metal layer directly or through an intermediate material;

providing a surface plasmon resonance by means of said acting;

reflecting partially said radiation under said surface plasmon resonance from said metal layer, with formation of a reflected beam;

using said reflected beam for producing a spatial distribution of electromagnetic field intensity, which is determined by said surface plasmon resonance;

recording parameters of said distribution, from which the examined characteristics are judged;

wherein said distribution is produced using interference of said reflected beam and, at least, one more radiation beam, which differs from said reflected beam in position or direction in space anywhere over its propagation path preceding to the interference, and on said boundary surface there is a layer that influences said surface plasmon resonance and has a pre-assigned variation in its thickness over said boundary surface, and a user controls sensitivity of parameters of said distribution to the interaction of the medium under test with said sensitive material by choosing on said boundary surface an area, which accounts for said distribution by partially reflecting said radiation from this area under said surface plasmon resonance to form said reflected beam.

13. A method according to claim 12, wherein said layer that influences said surface plasmon resonance and has a pre-assigned variation in its thickness over said boundary surface is said metal layer.

14. A method according to claim 12, wherein said layer that influences said surface plasmon resonance and has a pre-assigned variation in its thickness over said boundary surface is the layer of said sensitive material.

15. An apparatus for examining biological, biochemical, chemical characteristics of media, including characteristics of media interactions with surfaces and superficial layers, which comprises:

a source of electromagnetic radiation, a transparent body, a metal layer located on a boundary surface of the transparent body, a sensitive material placed on said boundary surface above said metal layer directly or through an intermediate material, a unit for introducing a volume or a constituent of a medium under test into contact with said sensitive material, all being positioned so that radiation from said source is directed on said metal layer through said transparent body, thereby providing a surface plasmon resonance and partial reflection of said radiation under said surface plasmon resonance from said metal layer with formation of a reflected beam, and a means for producing, with the use of said reflected beam, a spatial electromagnetic field intensity distribution, which is determined by said surface plasmon resonance, a block for recording parameters of said distribution to obtain an output information signal, wherein said means comprises a facility or facilities for separating radiation, which comes from said source, into, at least, two beams that differ from each other in position or direction in space, one of the beams comprising radiation that participates in formation of said reflected beam, and bringing radiation from said two beams to an area where interference of radiation from these beams occurs, the position of said block being in a proper position with respect to the position of said area of interference, and said source allows a user to specify a discrete or continuous set of frequencies of the outgoing radiation, and said block allows said recording at a number, or within a band of frequencies that are within said set of frequencies.

16. An apparatus according to claim 15, wherein there is provided a number or a range of values of a first parameter relevant to said surface plasmon resonance, and said facility or facilities for separating radiation and bringing radiation are designed so that in said area of interference there are two different directions, orthogonal or tilted to each other, one being the direction of rapid change in the phase difference between two beams participating in said interference, and the other being the direction of the most rapid change of said first parameter.

17. An apparatus according to claim 16, wherein said first parameter is the angle of incidence of said radiation on said metal layer, and the apparatus further comprises a means to form a beam incident on or reflected from said metal layer, wherein said incident beam is divergent or convergent in the plane of incidence of the axial ray of the beam on said metal layer, and said facility for separating and bringing radiation is designed so as to split said divergent or convergent beam into two beams that have mutually orthogonal polarization directions and overlap within said area of interference, the direction of said split lying out of said plane of incidence.

18. An apparatus according to claim 16, wherein there is provided a variation in a second parameter, different from said first parameter and relevant to said surface plasmon resonance, said variation affecting the slope of interference fringes within said area of interference near the value of said first parameter that corresponds to said surface plasmon resonance, with respect to co-ordinate axes coincident with said two directions.

19. The apparatus of claim 18, wherein said variation is selected from the group consisting of frequency of said radiation, angle of incidence of said radiation on said metal layer, and thickness of a layer on said boundary surface.

20. The apparatus of claim 16, wherein said number or range of ratios is selected from the group consisting of frequency of said radiation, angle of incidence of said radiation on said metal layer, and thickness of a layer on said boundary surface.

21. An apparatus for examining biological, biochemical, chemical characteristics of media, including characteristics of media interactions with surfaces and superficial layers, which comprises:

a source of electromagnetic radiation, a transparent body, a metal layer located on a boundary surface of the transparent body, a sensitive material placed on said boundary surface above said metal layer directly or through an intermediate material, a unit for introducing a volume or a constituent of a medium under test into contact with said sensitive material, all being positioned so that radiation from said source is directed on said metal layer through said transparent body, thereby providing a surface plasmon resonance and partial reflection of said radiation under said surface plasmon resonance from said metal layer with formation of a reflected beam, and a means for producing, with the use of said reflected beam, a spatial electromagnetic field intensity distribution, wherein said distribution is determined by said surface plasmon resonance, a block for recording parameters of said distribution to obtain an output information signal, wherein said means comprises a facility or facilities for separating radiation, which comes from said source, into, at least, two beams, wherein said beams both comprise either radiation incident on, or reflected from, said metal layer and differ from each other in position or direction in space, one of the beams comprising radiation that participates in formation of said reflected beam, and bringing radiation from said two beams to an area where interference of radiation from these beams occurs, the position of said block being in a proper position with respect to the position of said area of interference.

22. An apparatus according to claim 21, wherein said facility for separating radiation is designed so as to yield said two beams with polarisation directions orthogonal to each other.

23. An apparatus for examining biological, biochemical, chemical characteristics of media, including characteristics of media interactions with surfaces and superficial layers, which comprises:

a source of electromagnetic radiation, a transparent body, a metal layer located on a boundary surface of the transparent body, a sensitive material placed on said boundary surface above said metal layer directly or through an intermediate material, a unit for introducing a volume or a constituent of a medium under test into contact with said sensitive material, all being positioned so that radiation from said source is directed on said metal layer through said transparent body, thereby providing a surface plasmon resonance and partial reflection of said radiation under said surface plasmon resonance from said metal layer with formation of a reflected beam, and a means for producing, with the use of said reflected beam, a spatial electromagnetic field intensity distribution, which is determined by said surface plasmon resonance, a block for recording parameters of said distribution to obtain an output information signal, wherein said means comprises a facility or facilities for separating radiation, which comes from said source, into, at least, two beams that differ from each other in position or direction in space, one of the beams comprising radiation that participates in formation of said reflected beam, and bringing radiation from said two beams to an area where interference of radiation from these beams occurs, the position of said block being appropriate to the position of said area of interference, and on said boundary surface there is a layer that has a pre-assigned variation in its thickness over said boundary surface and influences said surface plasmon resonance, and there is provided a means for choosing on said boundary surface an area, which accounts for said distribution by partially reflecting said radiation from this area under said surface plasmon resonance to form said reflected beam.

24. An apparatus according to claim 23, wherein said layer that has a pre-assigned variation in its thickness over said boundary surface and influences said surface plasmon resonance is said metal layer.

25. An apparatus according to claim 23, wherein said layer that has a pre-assigned variation in its thickness over said boundary surface and influences said surface plasmon resonance is the layer of said sensitive material.

26. An apparatus according to claim 23, wherein said means for choosing on said boundary surface an area is a means for scanning an irradiated area over said boundary surface.

* * * * *